(12) United States Patent
Karimian et al.

(10) Patent No.: US 6,506,929 B1
(45) Date of Patent: Jan. 14, 2003

(54) PROCESS TO MANUFACTURE SIMVASTATIN AND INTERMEDIATES

(75) Inventors: Khashayar Karimian, Mississauga (CA); Tim Fat Tam, Woodbridge (CA); Yong Tao, Brampton (CA); Yiwei Li, Etobicoke (CA); Gary Doucette, Downsview (CA)

(73) Assignee: Apotex Inc., Weston (CA)

( * ) Notice: Subject to any disclaimer, the term of this patent is extended or adjusted under 35 U.S.C. 154(b) by 0 days.

(21) Appl. No.: 09/719,606

(22) Filed: Apr. 24, 2001

(30) Foreign Application Priority Data

Jun. 18, 1998 (CA) .............................................. 2240983

(51) Int. Cl.⁷ .......................... C07C 69/74; C07C 61/28
(52) U.S. Cl. ....................... 560/119; 560/107; 560/256; 560/185; 560/119; 549/292; 562/501
(58) Field of Search ................................ 560/119, 256, 560/107, 185; 549/292; 562/501

(56) References Cited

U.S. PATENT DOCUMENTS

| | | | |
|---|---|---|---|
| 4,444,784 A | * | 4/1984 | Hoffman et al. |
| 4,450,171 A | | 5/1984 | Hoffman et al. ............ 424/279 |
| 4,582,915 A | * | 4/1986 | Sleteinger et al. |
| 4,820,850 A | | 4/1989 | Verhoeven |
| 4,916,239 A | | 4/1990 | Treiber ....................... 549/292 |
| 5,072,002 A | * | 12/1991 | Clive et al. |
| 5,159,104 A | | 10/1992 | Dabora et al. .............. 560/119 |
| 5,223,415 A | | 6/1993 | Conder et al. .............. 435/125 |
| 5,393,893 A | * | 2/1995 | Kubela et al. |

FOREIGN PATENT DOCUMENTS

| | | |
|---|---|---|
| CA | 1199322 | 1/1986 |
| CA | 1287063 | 7/1991 |
| CA | 1287639 | 8/1991 |

OTHER PUBLICATIONS

Clive et al, Journal of American Chemistry Society, 1988, v 110 pp. 6914–6916.*
Clive et al, Journal of American Chemistry Society, 1990, v 112, pp. 3018–3028.*
Article "Simvastatin: A review of its Pharmacology and Clinical Use" Mauro, et al, The Annuals of Pharmacotherapy, 1991, vol. 25, pp. 257–264.
Article "The Chemistry and Total Snthesis of Mevinolin and Related Compounds" Y. Chapleur, Recent Prog. Chem. Synth. Antiobiot, Relat. Microb. Product, 1993, p. 829–937.

* cited by examiner

*Primary Examiner*—Alan L. Rotman
*Assistant Examiner*—Hector M. Reyes
(74) *Attorney, Agent, or Firm*—Neil H. Hughes; Ivor M. Hughes; Marcelo K. Sarkis

(57) ABSTRACT

A process is disclosed for the preparation of simvastatin which enables highly regio selective C-methylation of the 2'-position group of lovastatin without requiring protection/deprotection of 13-OH of lovastatin and lactone ring opening/closure.

17 Claims, No Drawings

US 6,506,929 B1

PROCESS TO MANUFACTURE SIMVASTATIN AND INTERMEDIATES

TECHNICAL FIELD

This invention relates to novel processes for the manufacturing of simvastatin using lovastatin as staring material.

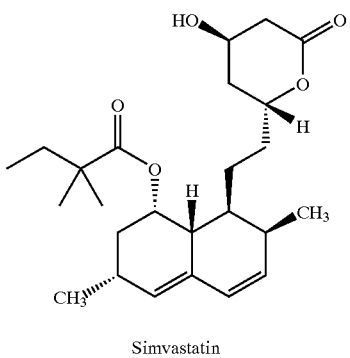

Simvastatin

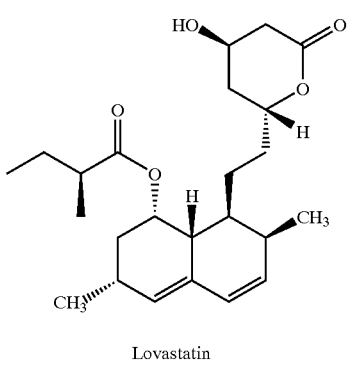

Lovastatin

BACKGROUND ART

Simvastatin is an antihypercholesterolemic agents which inhibits cholesterol biosynthesis by inhibiting the enzyme HMG-Co A reductase. Animal and clinical data suggest simvastatin is twice as potent as lovastatin. The pharmacology and clinical use of simvastatin has been reviewed (V. E. Mauro, J. L. MacDonald, DICP, The Annuals of Pharmacotherapy, 1991, 25, 257). The synthesis of simvastatin and related compounds was reviewed by Y. Chapleur in Recent Prog. Chem. Synth. Antibiot. Relat. Mircob. Product, 1993, p.829–937; editor: Lukacs, Gabor; publisher: Springer, Berlin, Germany.

Simvastain is an approved oral antihyperlipidemic medication and has been prepared by two general methods taught in Canadian patents 1,199,322 and 1,287,063. In a strict chemical sense, there are three potential methylation sites in lovastatin. These are 13-OH, 14-C and 2'-C. In its open form the 11-OH function provides an additional methylation site. A successful process requires the selective C-methylation of the 2'-position of side chain of lovastatin with minimum protection of other potentially reactive functional groups in lovastatin.

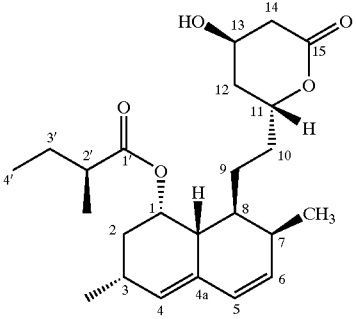

In the method taught in Canadian Patent 1,199,322, lovastatin is first treated with LiOH to give the triol VII which is re-lactonized to diol VIII. Selective silylation of the hydroxyl function at C-13 produces the silyl ether IX which is treated with 2-dimethylbutyryl chloride to give compound X. Desilylation of compound X leads to simvastatin VI (Scheme 1).

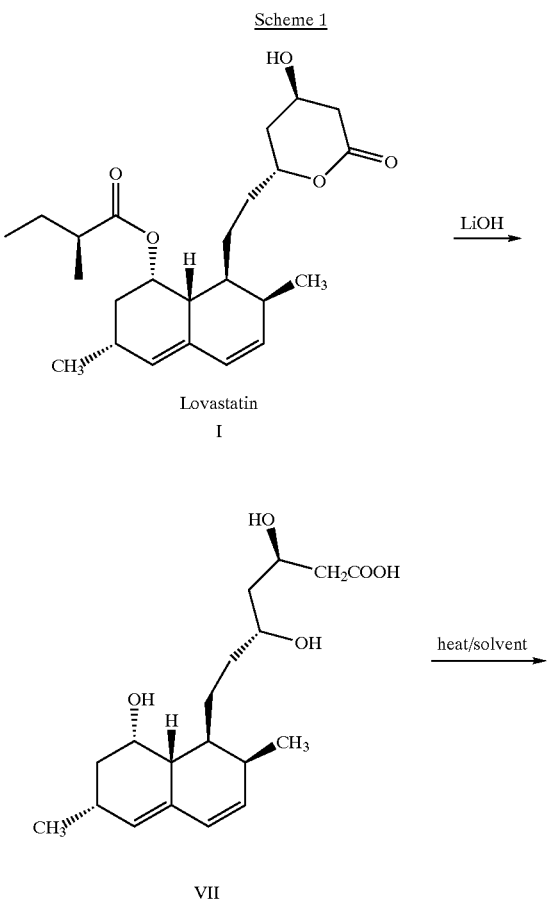

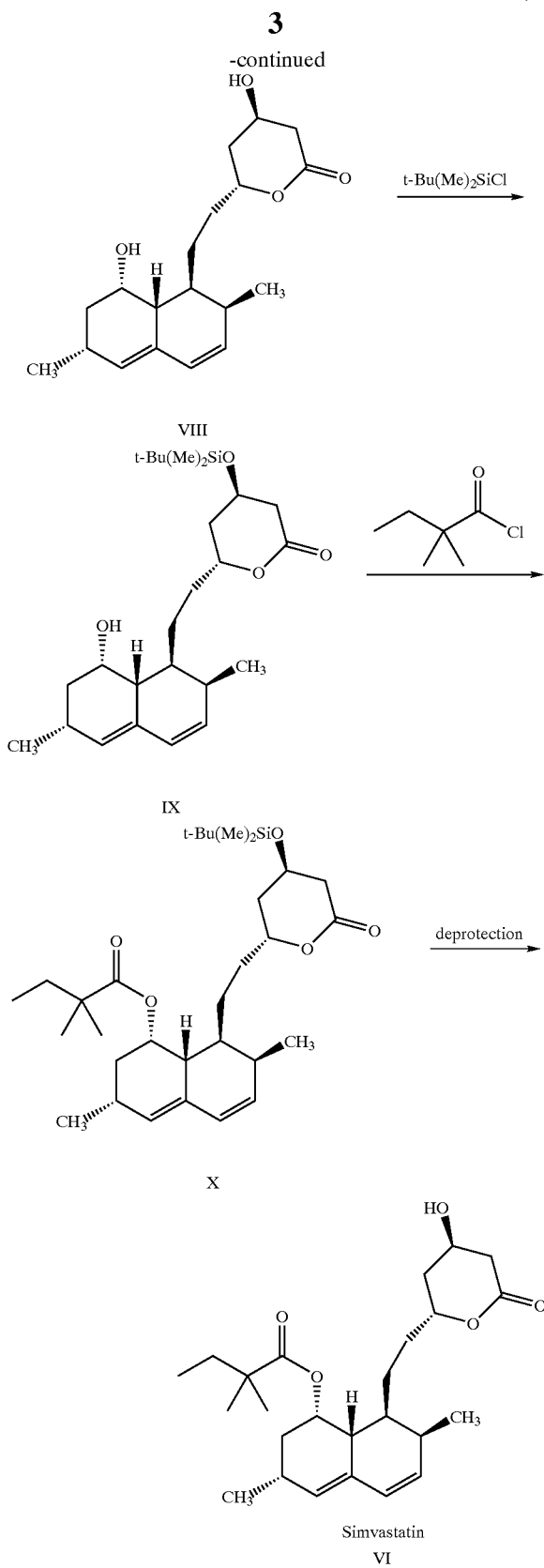

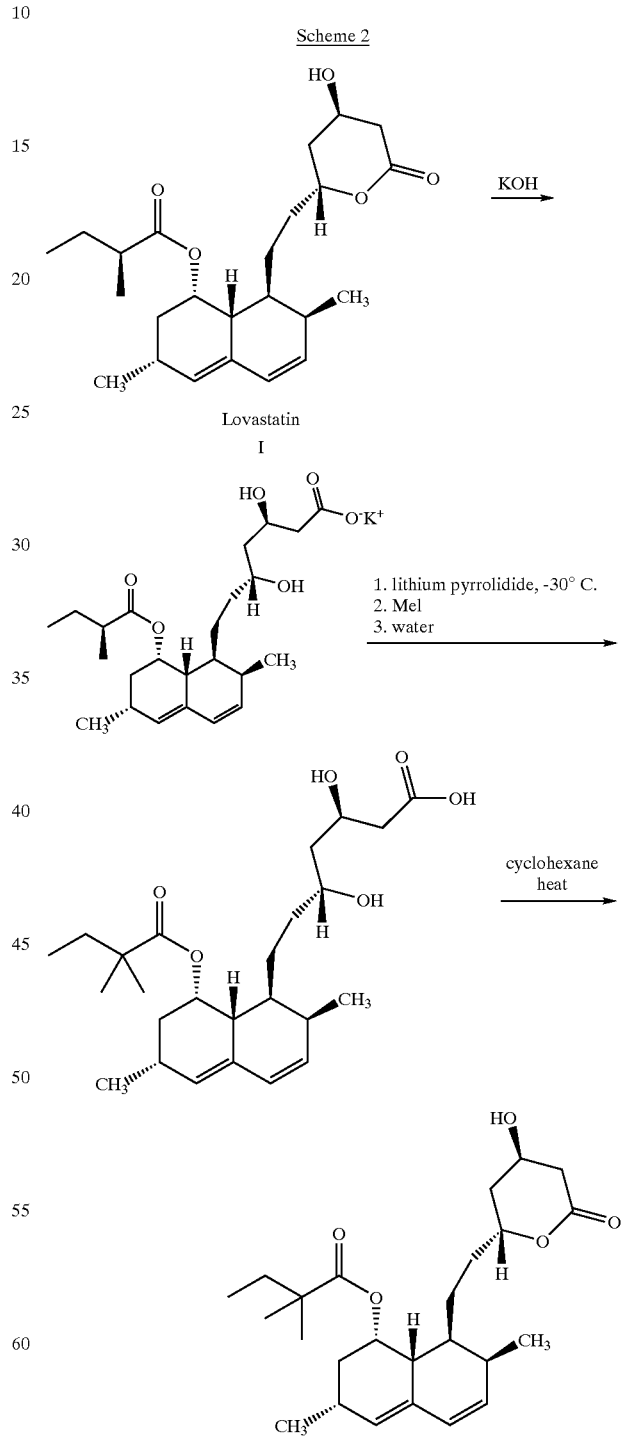

In U.S. Pat. No. 4,582,915, lovastatin is reacted with potassium hydroxide ant is converted into a potassium salt of a dihydroxy acid compound. The potassium salt is then enolized with lithium pyrrolidide and the enolate intermediate is alkylated with methyl iodide to produce a dihydroxy acid compound with the 2,2-dimethylated side chain. The dihydroxy acid is then heated and water is azeotropically removed to produce simvastatin (Scheme 2).

The overall yield is less than 40%. Variations of his method are disclosed in U.S. Pat. Nos. 5,159,104, 4,450,171, and 4,444,784.

The process is laborious and affords simvastatin only moderate yields. Furthermore, from the teachings of a subsequent U.S. Pat. No. 4,820,850 at column 1, lines 53 to 68 to column 2, lines 1 to 20 and its corresponding Canadian patent 1,287,063 at page 3, this process appears to have numerous disadvantages.

Canadian patent 1,287,063 states at page 3 that U.S. Pat. No. 4,582,915 "disclosed a novel route to the dimethyl-butyate side chain via direct alkylation of the α-carbon of the naturally available methylbutyrate side-chain using a metal amide and a methyl halide. However this process has been found to have certain disadvantages in the commercial manufacture of a pharmaceutical".

Repeated addition of the amide base and methyl halide are necessary to improve the yield of the alkylation step. This is costly, inefficient and time-consuming.

A selective hydrolysis is necessary to reduce the level of unmethylated starting material to less than 0.7%. This step is time consuming since the hydrolysis of unconverted starting material is very slow and normally requires 20 hours.

The overall yield of the process is low when the starting material is mevinolin.

In addition to unconverted starting material a number of other impurities are generated during the methylation and hydrolysis steps. These include, when the starting material is mevinolin, des-butyratemevinolin and bis-methylated compounds wherein the α-lactone carbon is methylated in addition to that on the δ-C-ester side chain, and a methyl ether wherein the ring oxygen of the lactone now in the open form has been methylated.

The purity of the final product isolated from the overall process is close to be unsatisfactory for use as a drug substance.

In an attempt to overcome the shortcomings of U.S. Pat. No. 4,582,915, another method disclosed in Canadian patent 1,287,063 was devised.

Canadian patent 1,287,063 teaches that the lactone ring of lovastatin is reacted with an amine to give the amide XI. The diol of the amide XI is protected as a disilyated ether XII. Alkylation of compound XII with methyl iodide and base produces compound XIII. Deprotection of the diol XIII, followed by lactonization afforded simvastatin (Scheme 3).

-continued

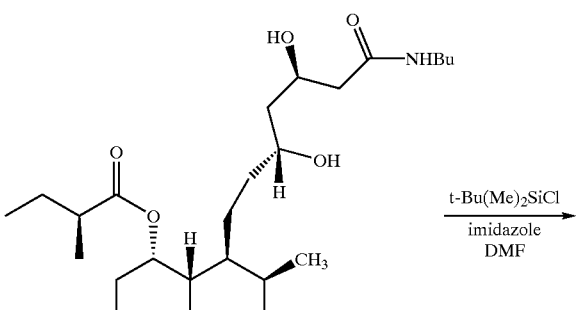

XI

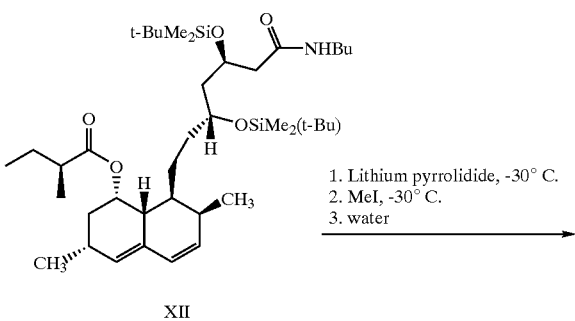

XII

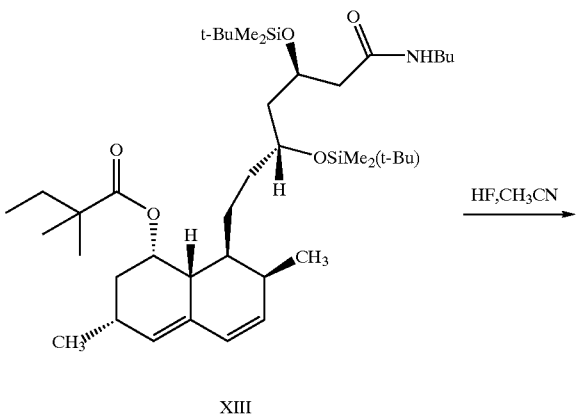

XIII

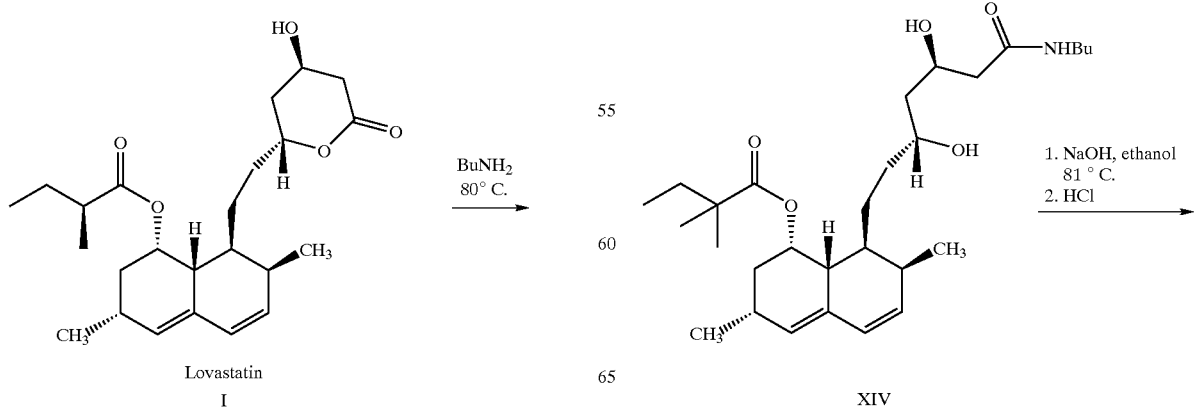

Scheme 3

Lovastatin
I

XIV

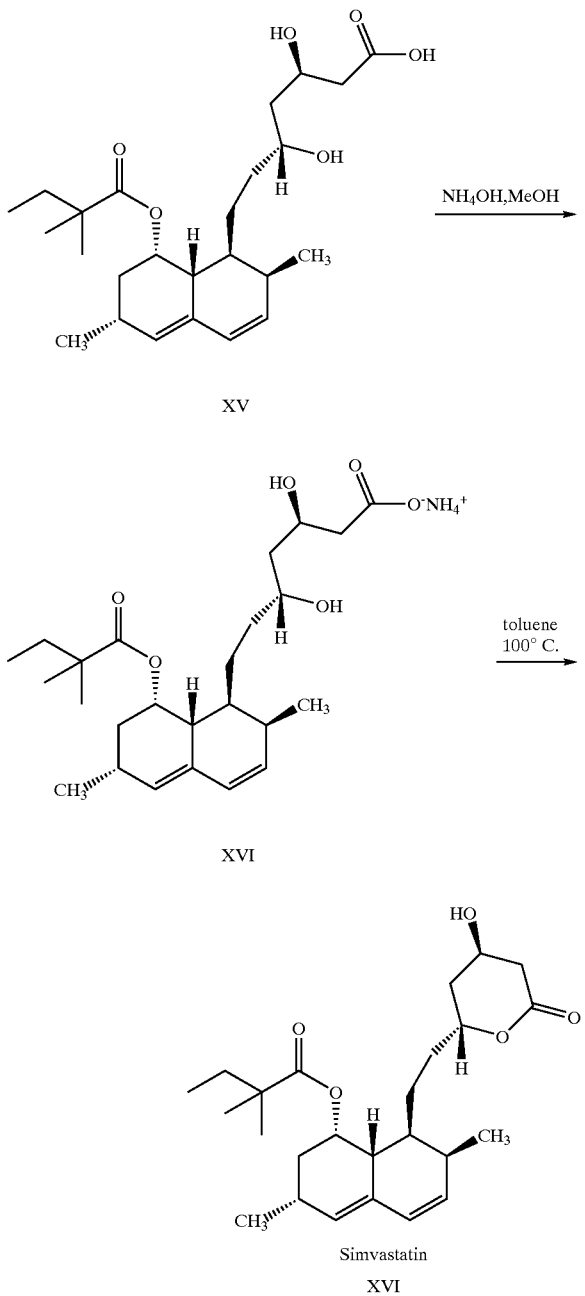

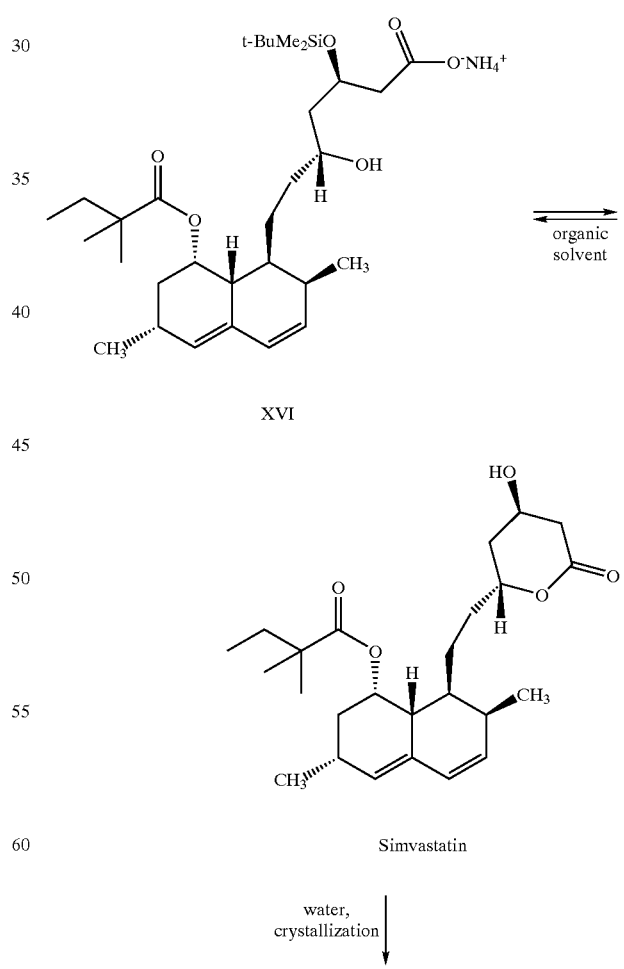

form of simvastatin XV is obtained. The dihydroxy acid compound XV is reacted with ammonium hydoxide to produce an ammonium salt XVI which is then relactonized by heating to produce simvastatin.

In an improved variation of this approach, phenyl boronic acid was used by Kubela, et al. for the protection of the diol resulting in a solid phenylboronate which can be subjected to purification by crystallization (U.S. Pat. No. 5,393,893).

Other variations of the method depicted in Scheme 3 are reported in U.S. Pat. Nos. 4,820,850, and 5,223,415.

In both methods discussed above the 13-OH is protected as a silyl ether. In the first process, the silyl group is removed after the introduction of the acyl group at the 1-OH position. In the second process, the silyl group is removed after the introduction the methyl group at 2'-position.

In Canadian patent 1,287,639 and its U.S. equivalent U.S. Pat. No. 4,916,239 a process for the lactonization of XVI produced as illustrated in Scheme 3 to simvastatin is disclosed. The ammonium salt XVI is suspended in an organic solvent with a strong acid catalyst. After the hydroxy acid-lactone equilibrium is established, water is gradually added to effect complete crystallization of simvastatin from the reaction medium (Scheme 4).

More particularly, Canadian patent 1,287,063 discloses that lovastatin is specifically reacted with butylamine to produce lovastatin buytlamide XI. The two hydroxy groups in the butylamide are protected with tert-butyldimethylsilyl chloride to produce a disilyated lovastatin buytlamide XII. The disilyated lovastatin buytlamide is enolized with lithium pyrrolidide and the enolate is alkylated with methyl iodide to produce a disilyated simvastatin butylamide on aqueous work up XIII. The silyl protecting groups are removed using hydrofluoric acid to produce simvastatin butylamide XIV. The simvastatin butylamide is hydrolysed using sodium hydroxide and following acidification, the dihydroxyacid -continued

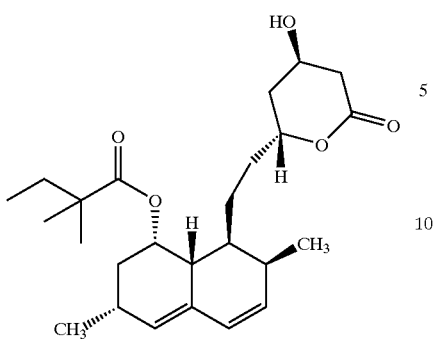

Simvastatin crystals

All the processes disclosed in the prior art involves numerous steps thereby contributing to the obtention of simvastatin in relatively low yield. Accordingly, a process that will overcome the disadvantages taught by the prior art will represent a considerable advance in the art.

The object of the present invention is to overcome these disadvantages. The process of the present invention is illustrated in Scheme 5.

Scheme 5

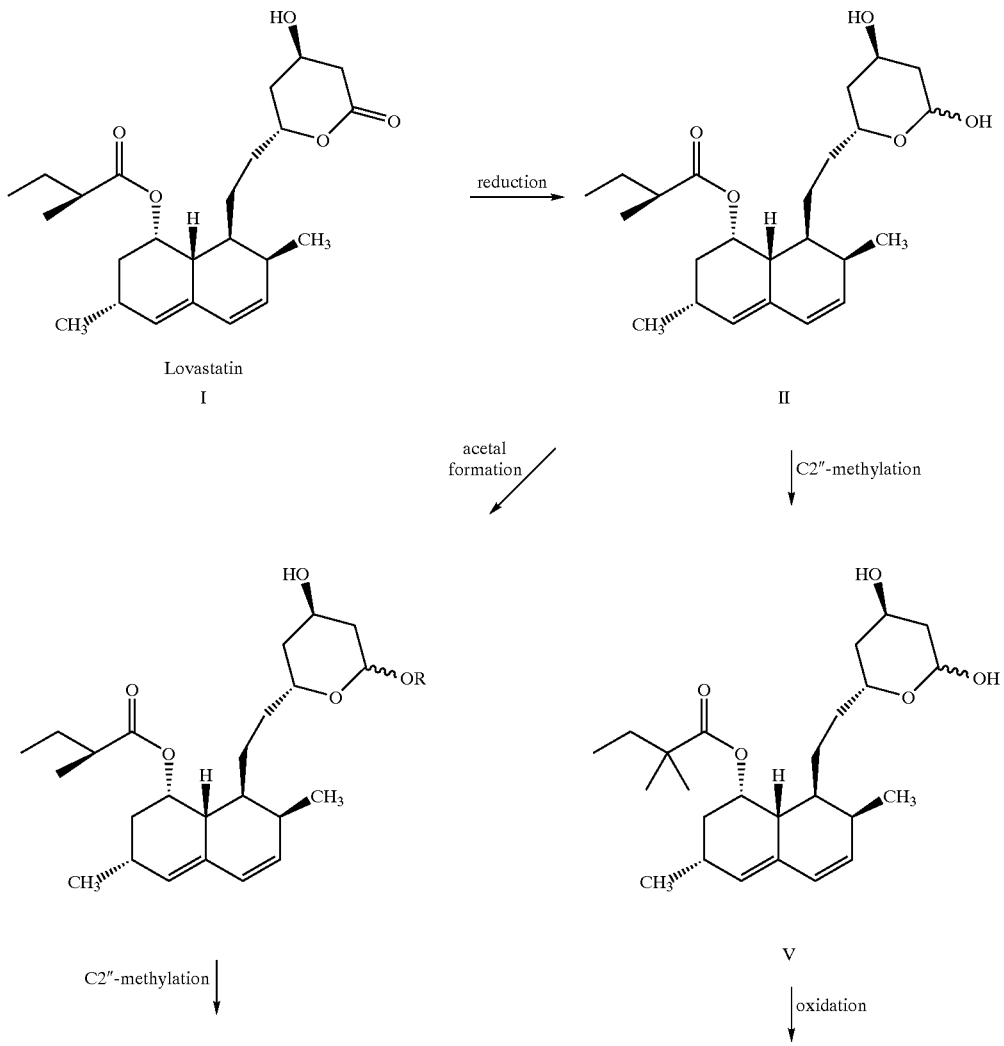

-continued

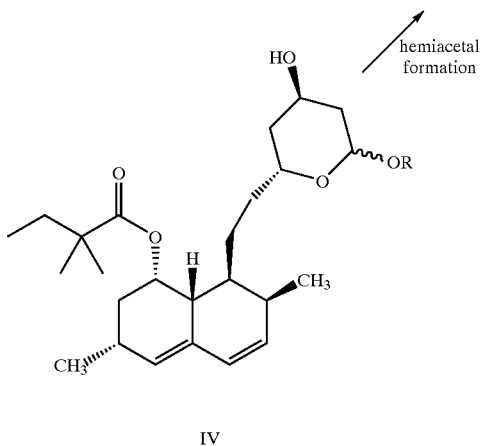

IV

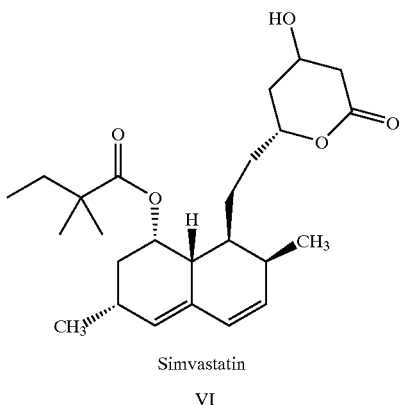

Simvastatin
VI

Accordingly, an object of the invention is to reduce the number of steps thereby allowing the production of simvastatin in higher yields (Process A, three steps).

Furthermore, by the process developed in the present invention, the C-methylation of the 2'-position group is highly regioselective and does not require the protection/deprotection of 13-OH group of lovastatin (processes A and B), nor does it involve the hydrolysis of the lactone moiety and re-lactonization.

Other advantages of the process of the present invention can be briefly listed:

(i) it avoids the use of expensive reagents such as tert-butyldimethylsilyl chloride and lachrymators such as 2,2-dimethylbutyryl chloride and hydrofluoric acid;

(ii) as the number of steps has been reduced, the process generates fewer impurities which simplifies the isolation of simvastatin of desirable level of purity;

(iii) it provides a simpler and a more economical method of manufacturing simvastatin and is therefore amendable to industrial scale production.

BRIEF SUMMARY OF INVENTION

A process for the manufacture of simvastatin which comprises:

(A) step 1. Selectively reducing the carbonyl function of the lactone moiety of lovastatin to a hemiacetal of formula II:

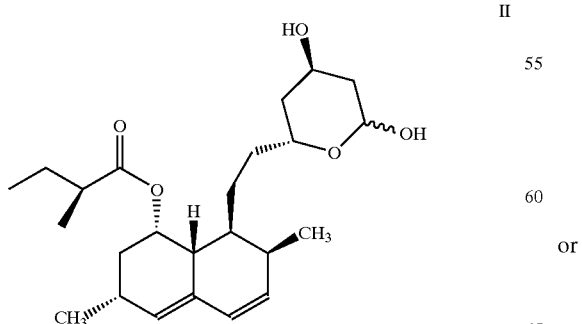

II step 2. reacting the compound of formula II with a strong base and methyl iodide in an inert solvent to give a compound of formula V:

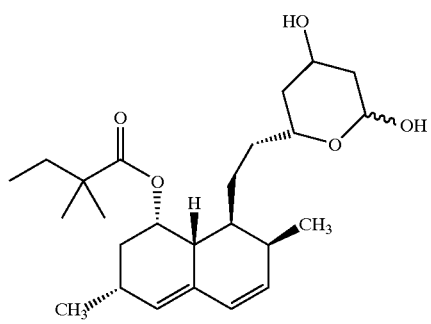

V step 3. oxidizing the compound of formula V to give simvastatin:

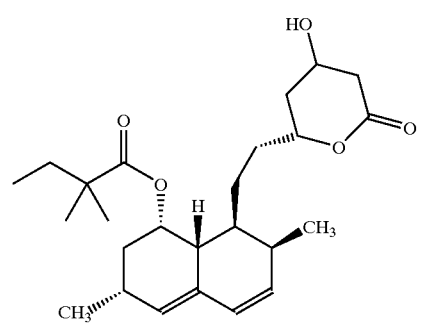

VI or (B) step 1. Selectively reducing the carbonyl function of the lactone moiety of lovastatin to a hemiacetal of formula II:

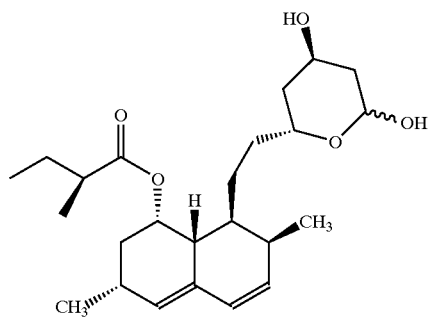

II step 2. reacting the compound of formula II with an alkanol ROH and an acid in which R is a lower alkyl or lower alkoxyalkyl to give a compound of formula III:

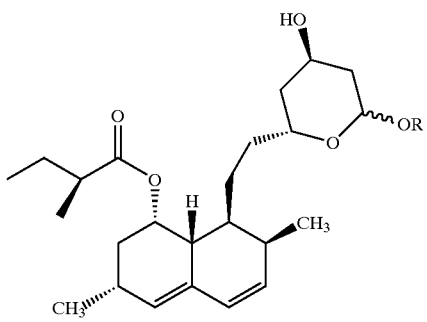

III step 3. reacting the compound of formula III with a strong base and methyl iodide in an inert solvet to give a compound of formula IV:

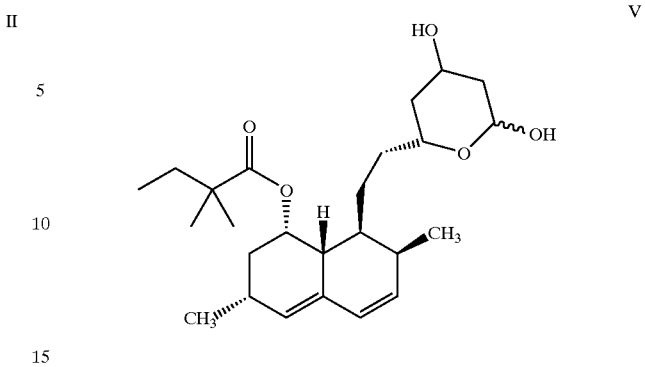

IV wherein R is as defined above;
step 4. reacting the compound of formula IV with a mild acid in an inert solvent to give a compound of formula V:

step 5. oxidizing the compound of formula V to give simvastatin:

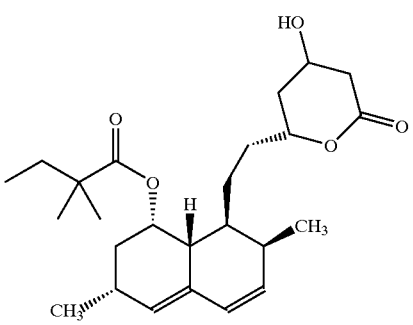

VI

DETAILED DESCRIPTION OF INVENTION

The carbonyl function of the lactone ring of lovastatin I is reduced in an inert solvent to the hemiacetal II (Scheme 5). Examples of such reducing agent are well documented in the art and include, for example: i-Bu$_2$AlH (Helv., 46, 2799; J. Org. Chem., 1965, 30, 3564; J. Am. Chem. Soc., 1969, 5675, 91; Synthesis 1975, 671); (Me$_2$CHCHMe)$_2$BH(J. Org. Chem., 1986, 51, 5032; Tet. Lett. 1987, 1073); NaH$_2$Al (OCH$_2$CH$_2$OCH$_3$)$_2$ (Synthesis, 526, 1976). The most preferred reagent for this reduction is i-Bu$_2$AlH. The reaction is normally carried out in an inert solvent such as toluene, heptane, dichloromethane or tetrahydrofuram. The reaction temperature is normally kept at −35° C. to −78° C. The reduction reaction of lovastatin would be expected to afford the tetraol XVII and its partial reduction the diol XVII. However, lovastatin undergoes selective reduction with i-Bu$_2$AlH to give the hemiacetal II as the the main product. The preferred condition requires the use of 2.0 to 2.5 equivalents of i-Bu$_2$AlH, in inert solvent such as toluene, heptane, tetrahydrofuran, preferably tetrahydrofuran, at −35° C. for a period of 1–4 hrs, preferably for 2 hrs. The hemiacetal II is isolated by conventional means.

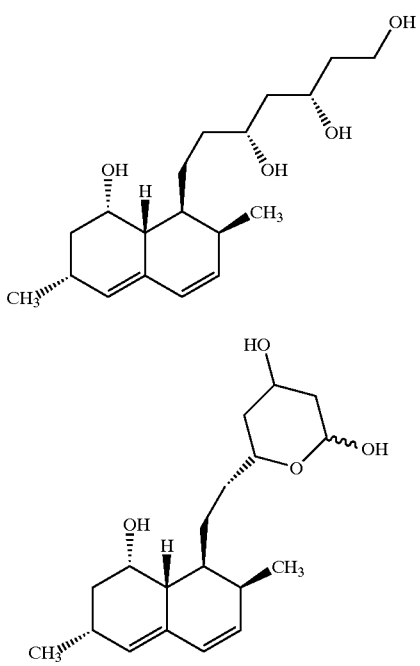

In Process A, the hemiacetal II is directly methylated at the C2' position with methyl iodide in an inert solvent such as tetrahydrofuran, 1,2-dimethoxyethane, in the presence of a strong base to give the hemiacetal V. Example of such bases include: lithium diisopropylamide, lithium hexamethyldisilylamide, lithium pyrrolidine, sodium hexamethyldisilylamide, and potassium diisopropylamide. The most preferred condition for this transformation requires the mixing of n-butyl lithium and pyrrolidine at about −25° C. in an inert solvent such as tetrahydrofuran to generate the lithium amide which is then further cooled to a lower temperature, preferably −35° C., and added slowly to a solution of hemiacetal II in an inert solvent such as tetrahydrofuran at the same temperature so as to maintain to internal temperature at −30 to −35° C. This is followed by the addition of methyl iodide. The alkylation product can be isolated by conventional methods.

In process B, the hemiacetal II is converted to acetal III with catalytic amounts of HCl in an alcohol of formula ROH wherein R is lower alkyl. The most preferred condition for this transformation requires the mixing of hemiacetal II and a solution of HCl in methanol at ambient temperatures for 1 to 4 hours. This gives an acetal of formula III wherein R is methyl. Alternatively, compound II is converted to a compound of formula III wherein R is lower alkoxyalkyl with 2-alkoxypropene, or alkoxyethene with pyridine hydrochloride or pyridine toluenesulfonic acid salt in an inert solvent such as methylene chloride. The terms lower alkyl and lower alkoxyalkyl refer to radicals having chains (straight or branched) consisting of $C_1$–$C_6$ carbon atoms.

Compound III reacts with methyl iodide in an inert solvent such as tetrahydrofuran, 1,2-dimethoxyethane, in the presence of a base to give the compound IV, in the same manner as described above for the conversion of compound II to V. The alkylation product can be isolated by conventional methods.

The resulting acetal IV is then converted to hemiacetal V with mild acid. The reaction takes place in 5% to 20% HCl in a mixture of water and inert solvent such as tetrahydrofuran or acetonitrile at 0 to 25° C. over a period of 1 to 4 hours. The product is isolated by conventional means.

Oxidation of acetal hemiacetal V, derived from either process (A or B), with silver carbonate on Celite in an inert solvent such as toluene at 80 to 120° C. affords simvastatin which is isolated in pure form by coventional means.

Process A consists of a three step synthesis of simvastatin from lovastatin. Since both 13-OH and 15-OH remain unprotected, the reaction consumes two additional moles of base in the C2'-methylation reaction.

Process B involves the conversion of hemiacetal II to acetal III, which upon C2'-methylation is converted to hemiacetal V. This is a common penultimate intermediate to both processes. Although process B is a five step synthesis, the conversion of II to III and III to V are simple and proceed in high yields.

Other potential approaches for the synthesis of simvastatin are shown in Schemes 6, 7 and 8. In Scheme 6, compound I may be reduced to the tetraol XVII. The 15-OH could be protected as a trityl ether, and the 11, 13-diol protected as an acetonide.

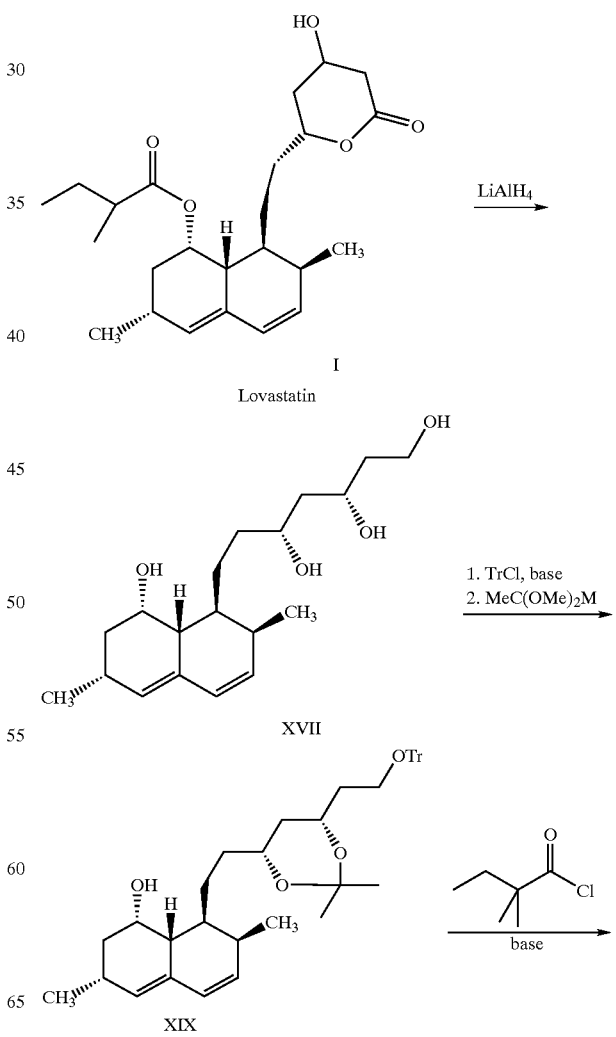

Scheme 6

-continued

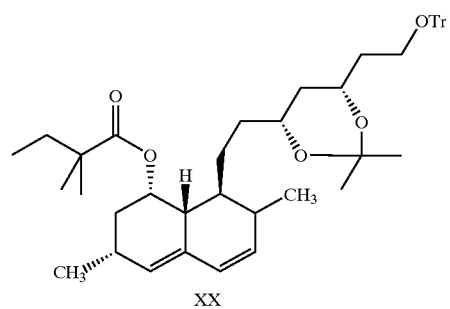
XX

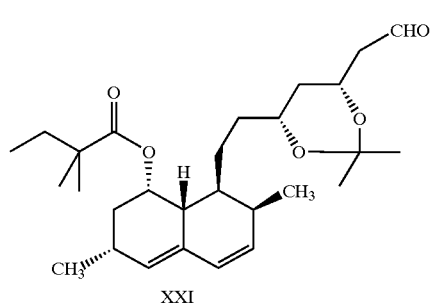
XXI

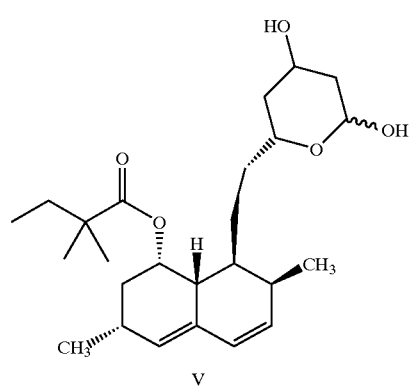
V

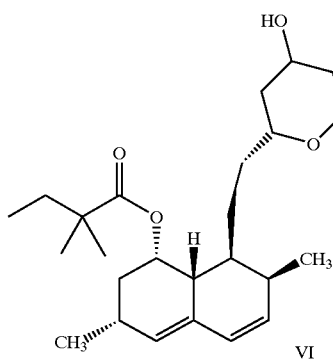
VI
Simvastatin

Acylation of the protected triol XIX would be expected to afford compound XX which upon deprotection at C-15 and oxidition would afford aldehyde XIX. Further deprotection of the C-11 and C-13 diol, followed by oxidation of the C-15 hemiacetal would provide simvastatin (VI).

In the approach shown in Scheme 7, compound I would be subjected to oxidation to afford ketone XXII. Ester hydrolysis of XXII would give XXIII, which upon reacylation would provide XXIV. Reduction of XXIV would be expected to afford simvastatin.

Scheme 7

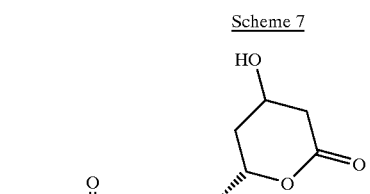
I
Lovastatin

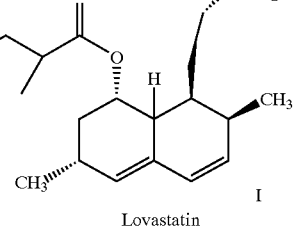

XXII

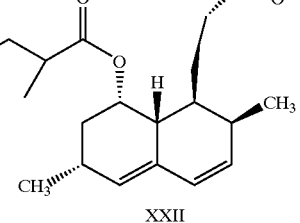

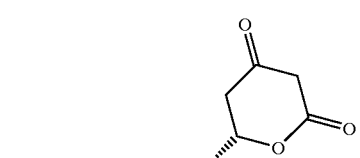
XXIII

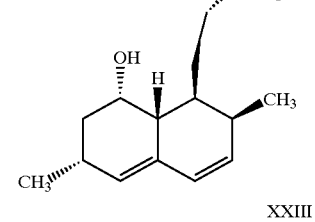

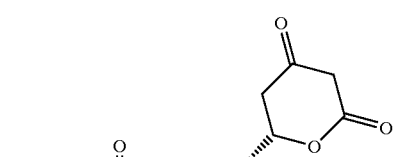
XXIV

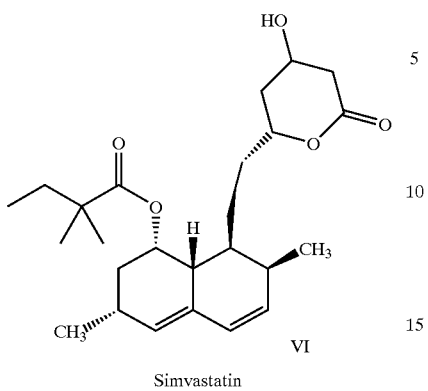

VI

Simvastatin

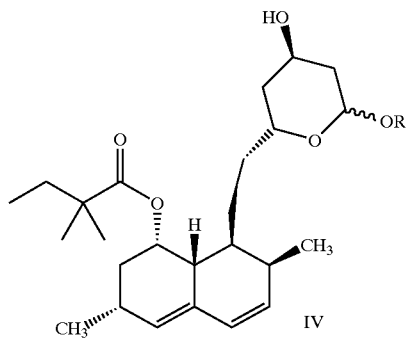

IV

Although these proposed syntheses do not fall within the scope of the two previously reported general processes for the synthesis of simvastatin, they involve manipulation of the lactone/ester function and therefore do not represent any advantage over the process of the present invention.

The following examples serve to illustrate certain aspects of the art thought in the present invention and should not be considered as limiting to the scope of the invention.

In the third approach shown in Scheme 8, compound III from our Process B could be hydrolyzed to give the diol XXV which upon selective acylation would provide compound IV. The later compound may subsequently converted to simvastatin according to the procedure outlined in Scheme 5.

EXAMPLE 1

[1S-[1α(R*),3α,7β,8β(2S*,4S*,6R*),8aβ,]]-1,2,3,7,8,8a-Hexahydro-3,7-dimethyl-8-[2-(tetrahydro-4,6-dihydroxy-2H-pyran-2-yl)ethyl]-1-naphthalenyl 2-Methylbutanoate and [1S-[1α(R*),3α,7β,8β(2S*,4S*,6S*),8aβ,]]-1,2,3,7,8,8a-Hexahydro-3,7-dimethyl-8-[2-(tetrahydro-4,6-dihydroxy-2H-pyran-2-yl)ethyl]-1-naphthalenyl 2-Methylbutanoate (II)

Diisobutylaluminum hydride (1.0 M solution in dichloromethane, 99.0 ml, 99 mmol) was added dropwise to a stirred and cooled (−35° C.) solution of lovastatin (20.0 g, 49.4 mmol) in tetahydrofuran (200 ml) in a period of 1 hours. Stirring was continued for 1 hour at −35° C. Celite (20 g) and sodium sulphate decahydrate (30 g) were added. The mixture was stirred for 20 min. Cooling bath was removed and stirring was continued for 1 hour. The mixture was filtered through a pad of Celite (8.0×1.5 cm) and the solid was washed with ethyl acetate. Evaporation of the combined filtrate gave crude hemiacetals II (19.0 g, yield 99%) as a white foam (HPLC purity>96%). This was used without further purification in the next step.

IR(KBr) 3439, 2850–3050, 1726, 1600 cm$^{-1}$; $^1$H NMR (CDCl$_3$, 300.133 MHz) δ 5.96 (d, J=9.6 Hz, 1H), 5.76 (dd, J=6.0, 9.4 Hz, 1H), 5.47 (br, 1H), 5.36–5.37 (m, 1H), 5.27 (br, 0.7H), 5.10 (d, 0.3H), 4.95 (d, 0.7H, OH), 4.41 (br, 1H, OH), 4.27 (br, 1H), 4.05–4.16 (m, 0.7H), 3.86 (d, 0.3H, OH), 3.71–3.80 (m, 0.3H), 2.28–2.41 (m, 3H), 2.21 (d, J=11.9 Hz, 1H), 1.58–1.98 (m, 9H), 1.10–1.47(m, 4H), 1.08 (d, J=7.0 Hz, 3H), 1.04 (d, J=7.4 Hz, 3H), 0.83–0.90 (m, 6H); $^{13}$C NMR(CDCl$_3$, 75.47 MHz) δ 177.0, 133.3, 131.7, 129.3, 128.1, 92.7, 92.3, 70.9, 68.0, 65.2, 64.8, 63.1, 41.4, 39.6, 38.2, 37.8, 37.4, 37.3, 36.5, 35.2, 32.8, 32.7, 32.6, 30.6, 30.5, 27.4, 26.7, 24.5, 24.3, 22.8, 16.1, 13.8, 11.6; mass, m/z 406 (calcd for C$_{24}$H$_{38}$O$_5$, m/z 406).

EXAMPLE 2

[1S-[1α(R*),3α,7β,8β(2S*,4S*,6R*),8aβ,]]-1,2,3,7,8,8a-Hexahydro-3,7-dimethyl-8-[2-(tetrahydro-4-hydroxy-6-methoxy-2H-pyran-2-yl)ethyl]-1-naphthalenyl 2-Methylbutanoate and [1S-[1α(R*),3α,7β,8β(2S*,4S*,6S*),8aβ,]]-1,2,3,7,8,8a-Hexabydro-3,7dimethyl-8-[2-(tetrahydro-4-hydroxy-6-methoxy-2H-pyran-2-yl)ethyl]-1-naphthalenyl 2-Methylbutanoate (III)

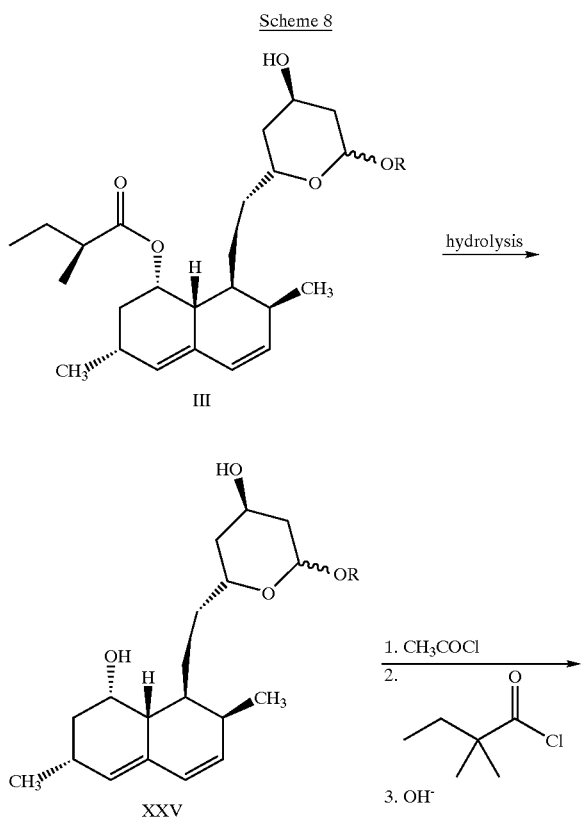

Scheme 8

Acetyl chloride (200 μL, 2.8 mmol) was added to a stirred solution of hemiacetals II (19.0 g, 46.7 mmol) in methanol (100 ml). The solution was stirred for 15 min at ambient temperature. Sodium bicarbonate (1.0 g) was added and the mixture was stirred for another 15 min. The mixture was filtered through a pad of Celite (5.5×1 cm) and washed with toluene. Evaporation of solvent of the filtrate gave crude acetals III (19.4 g, yield 98%) as a colorless syrup (HPLC purity >95%). This was used without further purification in the next step.

IR (KBr) 3478, 2850–3050, 1726 cm$^{-1}$; $^1$H NMR (CDCl$_3$, 300.133 MHz) δ 5.98 (d, J=9.7 Hz, 1 H), 5.78 (dd, J=6.0, 9.4 Hz, 1H), 5.50 (br, 1H), 5.32–5.36 (m, 1H), 4.81 (d, J=2.8 Hz, 0.3H), 4.69 (dd, J=2.1, 9.8 Hz, 0.7H), 4.26–4.28 (m, 0.7H), 4.01(br, 0.3H), 3.84–3.90(m, 0.3H), 3.69–3.77(m, 0.7H), 3.48 (s, 2.1H), 3.36 (s, 0.9H) 2.39–2.42 (m, 2H), 2.33 (q, J=6.9 Hz), 2.24 (dd, J=2.21, 11.9 Hz, 1H), 1.53–2.03 (m, 9H), 1.33–1.49(m, 4H), 1.09 (d, J=6.9 Hz, 3H), 1.06 (d, J=7.4 Hz, 3H), 0.84–0.91 (m, 6H); $^{13}$C NMR (CDCl$_3$, 75.47 MHz) δ 176.6, 133.4, 133.3, 131.8, 129.3, 128.2, 128.1, 99.2, 99.1, 70.8, 67.9, 67.8, 65.3, 64.1, 63.6, 56.0, 54.9, 41.4, 38.3, 37.3, 37.0, 36.8, 35.1, 33.0, 32.9, 32.6, 30.6, 27.4, 26.8, 24.7, 24.5, 22.7, 16.1, 13.8, 11.6; mass, m/z 420 (calcd for C$_{25}$H$_{40}$O$_5$, m/z 420).

EXAMPLE 3

[1S-[1α(R*),3α,7β,8β(2S*,4S*,6R*),8aβ,]]-1,2,3,7,8,8a-Hexahydro-3,7-dimethy-8-[2-(tetrahydro-4-hydroxy-6-methoxy-2H-pyran-2-yl)ethyl]-1-naphthalenyl 2,2-Dimethylbutanoate and [1S-[1α(R*),3α,7β,8β(2S*,4S*,6S*),8aβ,]]-1,2,3,7,8,8a-Hexahydro-3,7-dimethyl-8-[2-(tetrahydro-4-hydroxy-6-methoxy-2H-pyran-2-yl)ethyl]-1-naphthalenyl 2,2-Dimethylbutanoate (IV)

n-Butyl lithium (2.5M solution in hexane, 53.1 ml, 132.7 mmol) was added slowly to a stirred and cooled (−30° C.) solution of pyrrolidine (11.0 ml, 132.7 mmol) in dry tetrahydrofuran (100 ml). The solution was stirred at −25° C. for 1 hour. The above freshly prepared solution of lithium pyrrolidine was transferred slowly by cannula to a stirred and cooled (−35° C.) solution of the acetals III (18.7 g, 44.2 mmol) in dry tetrahydrofuran (200 ml). The mixture was stirred for 1 hour at −35° C. Iodomethane (6.9 ml, 110.6 mmol) was added slowly and the mixture was stirred for another 1 hour. Water (20 ml) was added to quench the reaction. After the cold bath was removed, saturated aqueous ammonium chloride solution (300 ml) was added and the mixture was stirred for 30 min. The mixture was extracted with toluene (3×250 ml). The combined organic extracts were washed with water (2×250 ml) and dried (Na$_2$SO$_4$). Evaporation of solvent gave crude acetal dimethylbutanoates IV (18.5 g, yield 96%) as a light brown syrup (HPLC purity >93%). This was used without further purification in the next step.

IR (KBr) 3519, 2850–3050, 1699 cm$^{-1}$; $^1$H NMR (CDCl$_3$, 300.133 MHz) δ 5.98 (d, J=9.6 Hz, 1H), 5.78 (dd, J=6.0, 9.4 Hz, 1H), 5.50 (m, 1H), 5.31–5.34 (m, 1H), 4.82 (d, J=2.6 Hz, 0.3H), 4.70 (dd, J=2.0, 9.7 Hz, 0.7H), 4.29–4.30 (m, 0.7H), 4.01–4.04 (m, 0.3H), 3.88–3.89(m, 0.31H), 3.69–3.78(m, 0.7 H), 3.61 (d, 1H, OH), 3.50 (s, 2.1H), 3.37 (s, 0.9H) 2.40–2.43 (m, 2H), 2.25 (d, J=11.9 Hz, 1H), 1.51–2.06 (m, 9H), 1.16–1.44(m, 4H), 1.12 (s, 6H), 1.07 (d, J=7.4 Hz, 3H), 0.89 (d, J=7.0 Hz, 3H), 0.83 (t, J=7.5 Hz, 3H); $^{13}$C NMR (CDCl$_3$, 75.47 MHz) δ 177.7, 133.3, 133.2, 131.8, 129.4, 128.3, 128.2, 99.2, 99.1, 70.8, 68.1, 68.0, 65.5, 64.2, 63.6, 56.1, 56.0, 42.9, 38.4, 37.5, 37.4, 37.1, 36.9, 35, 33.1, 33.0, 32.8, 32.7, 30.6, 27.3, 24.8, 24.7, 24.5, 23.0, 22.9, 13.8, 9.3; mass, m/z 434(calcd for C$_{26}$H$_{42}$O$_5$, m/z 434 ); elemental analysis, C: 71.60%, H: 9.70% (calcd for C$_{26}$H$_{42}$O$_5$, C: 71.84%. H: 9.75%).

EXAMPLE 4

[1S-[1α(R*),3α,7β,8β(2S*,4S*,6R*),8aβ,]]-1-1,2,3,7,8,8a-Hexahydro-3,7-dimethyl-8-[2-(tetrahydro-4,6-dihydroxy-2H-pyran-2-yl)ethyl]-1-naphthalenyl 2,2-Dimethylbutanonte and [1S-[1α(R*),3α,7β,8β(2S*,4S*,6R*),8aβ,]]-1,2,3,7,8,8a-Hexahydro-3,7-dimethyl-8-[2-(tetrahydro-4,6-dihydroxy-2H-pyran-2-yl)ethyl]-1-naphthalenyl 2,2-Dimethyl-butanoate (V from IV)

Hydrochloric acid (10%, 150 ml) was added to a stirred solution of acetal dimethylbutanoates IV (18.2 g, 45.1 mmol) in tetrahydrofuran (150 ml). The mixture was stirred for 1.5 hour at ambient temperature. Saturated aqueous sodium hydrogen carbonate solution was added slowly to adjust the reaction mixture to pH ca 7. The mixture was extracted with toluene (3×300 ml). The combined organic extracts were washed with brine (400 ml) and dried (Na$_2$SO$_4$). Evaporation of solvent gave crude hemiacetal dimethylbutanoates V (17.6 g, yield, quantitative) as a brown syrup (HPLC purity >75%). This was used without further purification in the next step. Part of the crude hemiacetal dimethylbutanoates V (0.6 g) was purified by flash chromatography over silica gel (2×12 cm) with ethyl acetate-heptane (1:1). The collected fractions were concentrated and crystallized from ethyl acetate-heptane to give a white powder (260 mg) which contained only one isomer.

m.p. 155–157° C.; IR (KBr) 3435, 3223, 2850–3050, 1714 cm$^{-1}$; $^1$H NMR (CDCl$_3$, 300.133 MHz) δ 5.98 (d, J=9.6 Hz, 1H), 5.78 (dd, J=6.1, 9.4 Hz, 1H), 5.47–5.49 (m, 1H), 5.35–5.36 (m, 1H), 5.29–5.32 (m, 1H), 4.67 (d, 1H, OH), 4.10–4.20 (m, 2H), 3.63 (d, 1H, OH), 2.35–2.41 (m, 2H), 2.20–2.25 (m, 1H), 1.15–1.98 (m, 13H), 1.12 (s, 3H), 1.11 (s, 3H), 1.07 (d, J=7.5 Hz, 3H), 0.86 (d, J=7.1 Hz 3H). 0.82 (t, J=7.5 Hz, 3H); $^{13}$C NMR (CDCl$_3$, 75.47 MHz) δ178.1, 133.2, 131.7, 129.4, 128.2, 92.9, 68.2, 64.9, 63.0, 43.0, 38.3, 37.8, 36.4, 35.2, 33.0, 32.8, 30.5, 27.2, 24.7, 24.6, 24.3, 23.0, 13.9, 9.2; mass, m/z 420 (calcd for C$_{25}$H$_{40}$O$_5$, m/z 434); elemental analysis, C: 71.27% H: 9.42% (calcd for C$_{26}$H$_{42}$O$_5$, C: 71.38%, H: 9.49%).

EXAMPLE 5

[1S-[1α(R*),3α,7β,8β (2S*,4S*,6R*),8aβ,]]-1,2,3,7,8, 8a-Hexahydro-3,7-dimethyl -8-[2-(tetrahydro-4,6-dihydroxy-2H-pyran-2-yl)ethyl-1-naphthalenyl 2,2-Dimethylbutanoate and [1S-1α(R*),3α,7β,8β(2S*,4S*,6S*),8aβ,]]-1,2,3,7,8,8a-Hexahydro-3,7-dimethyl-8-[2-(tetrahydro-4,6-dihydroxy-2pyran-2-yl)ethyl]-1-naphthalenyl 2,2-Dimethyl-butanoate (V from II)

n-Butyl lithium (2.5 M solution in hexane, 37.8 ml, 95.4 mmol) was added slowly to a stirred and cooled (−30° C.) solution of pyrrolidine (8.0 ml, 95.4 mmol) in dry tetrahydrofuran (150 ml), The solution was stirred at −25° C. for 1 hour. The above fresh made lithium pyrrolidine was transferred slowly by cannula to a stirred and cooled (−35° C.) solution of the hemiacetals II (8.6 g, 21.2 mmol) in dry tetrahydrofuran (150 ml). The mixture was stirred for 1 hour at −35° C. Iodomethane (4.8 ml, 76.5 mmol) was added slowly and the mixture was stirred for another 1 hour. Water (20 ml) was added to quench the reaction. After the cold bath was removed, saturated aqueous ammonium chloride solution (200 ml) was added and the mixture was stirred for 30 min. The mixture was extracted with ethyl acetate (3×250 ml). The combined organic extracts were washed with brine (2×200 ml) and dried (MgSO₄). Evaporation of solvent gave crude acetal dimethylbutanoates V (8.8 g, quantitative) as a light brown syrup (HPLC purity >85%). This was used without further purification in the next step.

EXAMPLE 6

[1S-[1α(R*),3α,7β,8β(2S*,4S*),8aβ,]]-1,2,3,7,8,8a-Hexahydro-3,7-dimethyl-8-[2tetrahydro-4-hydroxy6-oxo-2H-pyran-2-yl)ethyl]-1-naphthalenyl 2,2-Dimethylbutanoate (Simvastatin, VI)

Celite (29.4 g) and silver carbonate (14.7 g, 53.2 mmol) were added to a solution of crude hemiacetal dimethylbutanoate V (15.0 g, 35.7 mmol) in toluene (300 ml). The mixture was refluxed in a preheated oil bath (130° C.) for 2 hours. The reaction was protected from light. After cooling to room temperature, the mixture was filtered through a pad of Celite (8×2 cm) and washed with ethyl acetate (400 ml). The combined filtrates were treated with charcoal (3.0 g) for 30 min. at ambient temperature. The suspension was filtered through a pad of Celite (8×2 cm) and washed with ethyl acetate (200 ml). Evaporation of the solvent of the combined filtrate gave a light yellow oil. Crystallization of the crude product from cyclohexane-heptane(1:1) gave simvastatin (7.2 g, yield 48%) as a white solid. Its analytical data including TLC, HPLC, ¹H NMR, ¹³C NMR and IR are identical with an authentic sample.

What is claimed is:

1. A process for the manufacture of simvastatin which comprises:

Process (A) step 1. selectively reducing the carbonyl function of the lactone moiety of lovastatin to a hemiacetal of formula II:

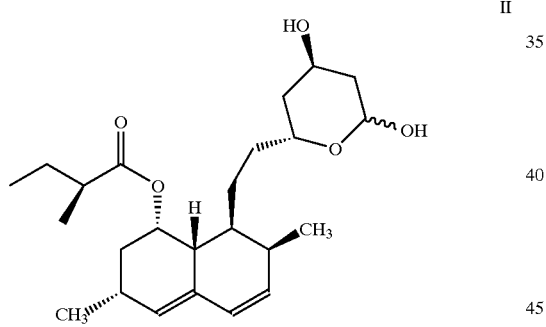

II step 2. reacting the compound of formula II with a strong base and methyl iodide in an inert solvent to give a compound of formula V:

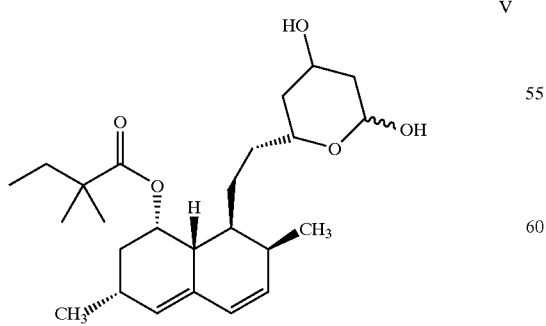

V step 3. oxidizing the compound of formula V to give simvastatin:

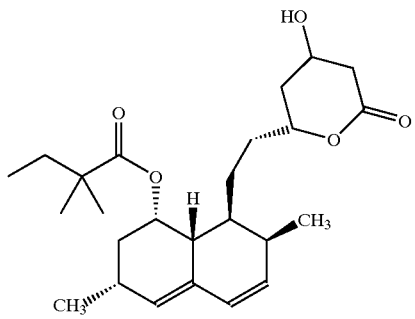

VI

Process (B) step 1. selectively reducing the carbonyl function of the lactone moiety of lovastatin to a hemiacetal of formula II:

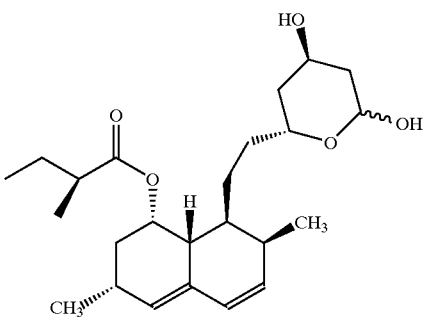

II step 2. reacting the compound of formula II with an alkanol ROH and an acid in which R is a lower alkyl or lower alkoxyalkyl to give a compound of formula III:

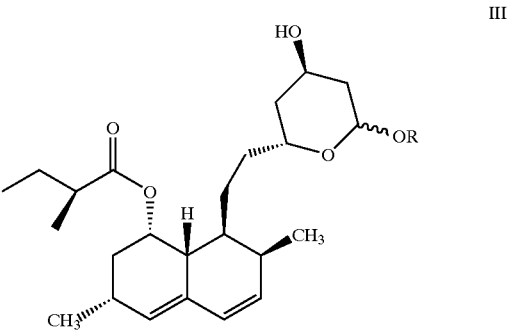

III step 3. reacting the compound of formula III with a strong base and methyl iodide in an inert solvent to give a compound of formula IV:

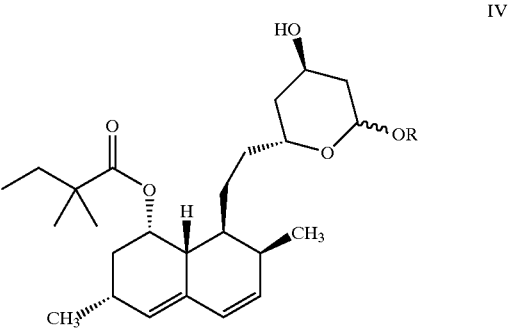

IV wherein R is as defined above:

step 4. reacting the compound of formula IV with a mild acid in an inert solvent to give a compound of formula V:

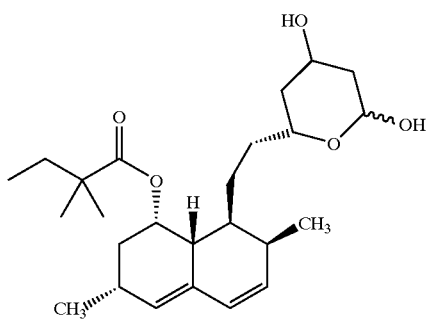

step 5. oxidizing the compound of formula V to give simvastatin:

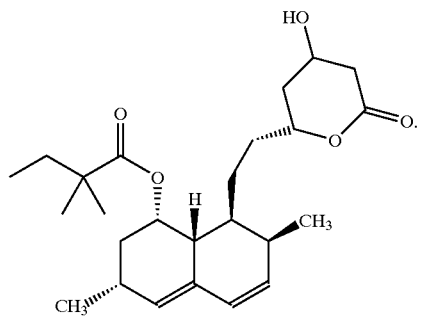

2. The process of claim 1 which is A.

3. The process of claim 1 which is B.

4. The process of claim 1, 2 or 3 wherein the selective reduction in step 1 is conducted with 2.0 to 2.5 equivalents diisobutylaluminium hydride in an inert solvent at a temperature in the range of −35° C. to 78° C. for about 2 hours.

5. The process of claim 4 wherein the inert solvent is selected from the group consisting of toluene, heptane, dichloromethane or tetrahydrofuran.

6. The process of claim 1(A) or 2 in which the strong base in step 2 is selected from the group consisting of lithium diisopropylamide, lithium hexamethyldisilylamide, lithium pyrrolidine, soldium hexomethyldisilylamide or potassium diisopropylamide.

7. The process of claim 1(A) or 2 in which step 2 is conducted in an inert solvent.

8. The process of claim 7 wherein the inert solvent is tetrahydrofuran or 1,2-dimethoxyethane.

9. The process of claim 1(B) or 3 in which the alkanol in step 2 is methanol.

10. The process of claim 1(B) or 3 in which the acid in step 2 is hydrochloric acid.

11. The process of claim 1(B) or 3 in which the strong base in step 3 is selected from the group consisting of lithium diisopropylamide, lithium hexamethyldisilylamide, lithium pyrrolidine, sodium hexomethyldisilyl-amide or potassium diisopropylamide.

12. The process of claim 1(B) or 3 in which the mild acid in step 4 is a solution of 5% to 20% of hydrochloric acid.

13. The process of claim 12 wherein the inert solvent is tetrahydrofuran or acetonitrile.

14. The process of claim 1, 2 or 3 wherein the oxidizing agent is silver carbonate on Celite.

15. The process of claim 14 wherein the oxidation is conducted in the presence of an inert solvent.

16. A compound of formula IV:

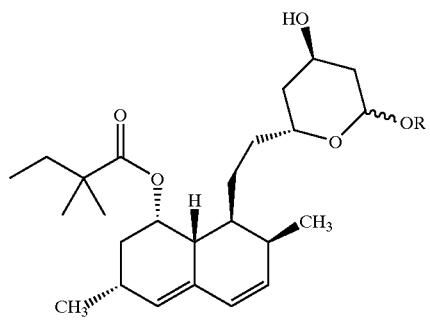

wherein R is lower alkyl or lower alkoxyalkyl.

17. The compound:

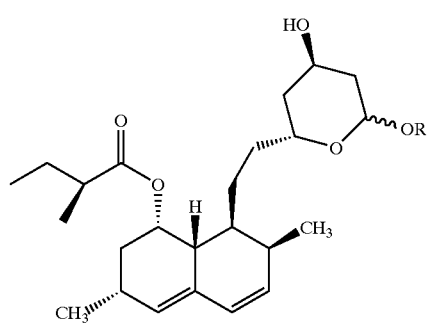

where R is lower alkyl or lower alkoxyalkyl.

* * * * *

UNITED STATES PATENT AND TRADEMARK OFFICE
CERTIFICATE OF CORRECTION

PATENT NO. : 6,506,929 B1
DATED : January 14, 2003
INVENTOR(S) : Khashayar Karimian et al.

It is certified that error appears in the above-identified patent and that said Letters Patent is hereby corrected as shown below:

<u>Title page,</u>
Item [56], References Cited, OTHER PUBLICATIONS, "Article The Chemistry" reference, the word "Snthesis" should be changed to -- Synthesis --.

<u>Column 7,</u>
Line 51, the word "XVI" should be changed to -- VI --.

<u>Column 8,</u>
Line 30, the word "t-BuMe$_2$SiO" should be changed to -- HO --.

<u>Column 9,</u>
Last figure, please insert -- III --.

<u>Column 11,</u>
Last figure, please insert -- II --.

<u>Column 13,</u>
Line 41, the word "solvet" should be changed to -- solvent --.

<u>Column 14,</u>
Line 55, the word "tetrahydrofuram" should be changed to -- tetrahydrofuran --.
Line 58, the word "XVII" should be changed to -- XVIII --.

<u>Column 25,</u>
Line 42, the word "78ºC" should be changed to -- -78ºC --.

Signed and Sealed this

Fourth Day of May, 2004

JON W. DUDAS
*Acting Director of the United States Patent and Trademark Office*